US005620838A

United States Patent [19]

Chen et al.

[11] Patent Number: 5,620,838
[45] Date of Patent: Apr. 15, 1997

[54] PHOTOGRAPHIC ELEMENTS CONTAINING DIRECTLY DISPERSIBLE UV ABSORBING POLYMERS AND METHOD OF MAKING SUCH ELEMENTS AND POLYMERS

[75] Inventors: Tienteh Chen, Penfield; Hwei-Ling Yau, Rochester; Edward Schofield, Penfield, all of N.Y.

[73] Assignee: Eastman Kodak Company, Rochester, N.Y.

[21] Appl. No.: 361,276

[22] Filed: Dec. 21, 1994

[51] Int. Cl.$^6$ .................. G03C 1/815; C07D 249/16; C07D 403/00
[52] U.S. Cl. .................. 430/512; 430/931; 252/589; 524/91; 548/260
[58] Field of Search .................. 430/512, 931; 252/589; 524/91; 548/260

[56] References Cited

U.S. PATENT DOCUMENTS

| | | | |
|---|---|---|---|
| 2,870,012 | 1/1959 | Godowski et al. | 96/97 |
| 3,813,255 | 5/1974 | Mannens et al. | 430/512 |
| 4,340,669 | 7/1982 | Monbaliu et al. | 430/512 |
| 4,511,647 | 4/1985 | Hirano et al. | 430/381 |
| 4,576,911 | 3/1986 | Mizukura et al. | 430/548 |
| 5,360,710 | 11/1994 | Chen et al. | 430/548 |
| 5,384,235 | 1/1995 | Chen et al. | 430/512 |
| 5,385,815 | 1/1995 | Schofield et al. | 430/512 |

*Primary Examiner*—Richard L. Schilling
*Attorney, Agent, or Firm*—Edith A. Rice

[57] ABSTRACT

A polymeric UV absorbing compound which comprises UV absorbing monomeric units of at least 0.05 weight percent of ionic units which have an ionizable group which is ionized at all pH values between 5 to 10. Photographic elements which contain such polymeric compounds and methods of making such polymers and photographic elements, are also provided. The polymeric UV absorbing compounds are directly dispersible in water.

26 Claims, No Drawings

PHOTOGRAPHIC ELEMENTS CONTAINING DIRECTLY DISPERSIBLE UV ABSORBING POLYMERS AND METHOD OF MAKING SUCH ELEMENTS AND POLYMERS

FIELD OF THE INVENTION

This invention relates to photographic elements which contain particular polymeric UV absorbing compounds, and methods of making such elements and polymeric UV absorbing compounds.

BACKGROUND OF THE INVENTION

Typical photographic elements use silver halide emulsions, the silver halide having a native sensitivity to ultraviolet UV radiation ("UV"). UV radiation is usually regarded as anything less than about 400 nm. Such UV sensitivity is usually undesirable in that it produces an image on the photographic element which is not visible to the human eye. In addition, in the case of color photographic elements, in particular, color dye images formed on the light sensitive emulsion layers by color development easily undergo fading or discoloration due to the action of UV. Also, color formers, or so-called couplers, remaining in the emulsion layers are subject to the action of UV to form undesirable color stains on the finished photographs. The fading and the discoloration of the color images are easily caused by UV of wavelengths near the visible region, namely, those of wavelengths from 300 to 400 nm. For the foregoing reasons, photographic elements typically incorporate a UV absorbing material particularly in an upper layer.

Many types of UV absorbing materials have been described previously, and include those described in U.S. Pat. Nos. 3,215,530, 3,707,375, 3,705,805, 3,352,681, 3,278,448, 3,253,921, and 3,738,837, 4,045,229, 4,790,959, 4,853,471, 4,865,957, and 4,752,298, and United Kingdom Patent 1,338,265. Known UV absorbing materials often have many undesirable characteristics. For example, they tend to color and form stains due to their insufficient stability to UV, heat, and humidity. Also, a high-boiling organic solvent is usually required for the emulsification of the UV absorbing agents, which softens the layer and substantially deteriorates interlayer adhesion. In order to prevent these problems, a large amount of gelatin has been used in the layer containing the UV absorbent, resulting in a layer which may be unstable. Alternatively, a separate gelatin protective layer was provided over the UV absorbent containing layer. Such approach results in an undesirable thickening of the element. Furthermore, previously known UV absorbing agents, when provided in the uppermost layer of a photographic element, often migrate and crystallize at the surface of the layer. Thus, a gel overcoat would be used to minimize this undesirable blooming phenomenon. Furthermore, the droplets of such UV absorbing materials, when prepared by the conventional emulsification method described above, usually have particle sizes greater than 200 nm thereby producing light scattering with resulting deterioration of the element's photographic properties. The toxicity of such UV absorbing agents has also become an important issue recently.

It is known that polymer latexes obtained by polymerization of UV absorbing monomers can be utilized as a UV absorbing agents which do not have such disadvantages. Two processes for adding polymeric UV absorbing agents in the form of a latex to hydrophilic colloid compositions, such as gelatin/water compositions, have been known. The first process comprises adding a latex prepared by emulsion polymerization directly to a gelatin-containing silver halide emulsion. Emulsion polymerization is well known in the art and is described in :(1) F. A. Bovey, Emulsion Polymerization, Interscience Publishers Inc., New York, 1955. (2) C. Schildknecht and I. Skeist, Polymerization Process, pp.143–197, Wiley-Interscience Publication, NY, 1977 and (3) R. Fitch, Polymer Colloid II, Plenum Press, NY, 1980. This is the most desirable process because the polymer latex can be prepared in one step.

However, the possibility of using emulsion polymerization is limited by the fact that the monomers need be dispersed in liquid form while most UV absorbing monomers are solid at room temperature and have very low water solubilities.

As the term emulsion polymerization implies, it is first necessary for the monomer to be dispersed in the form of oil droplets in the aqueous phase according to the theory that Harkins proposed on the emulsion polymerization of styrene, and that qualitatively complies with the emulsion polymerization of most other liquid monomers (J. Am. Chem. Soc. 69, 1428(1947); J. Polymer Sci. 5, 217(1950)). When a water-immiscible, organic monomer is dispersed in water in the presence of a surface-active emulsifying agent, the monomer is mainly dispersed in droplets of a diameter of about 1µ and these droplets are stabilized by emulsifier (or surfactants). A little amount of the monomer, however, is solubilized in micelles formed by emulsifier. Radicals formed by decomposition of a polymerization catalyst ,for example persulfate, initiate the polymerization solely in the micelles, which are thereby transformed progressively in polymer particles swollen by monomer. The monomer in these particles is gradually used up as polymerization proceeds but is continuously renewed by diffusion from the monomer droplets through the aqueous phase. The monomer droplets are thus acting as highly dispersed reservoirs of monomers.

From the Harkins theory, it is not difficult to understand that solid monomers, with melting point higher than the polymerization temperature and with relatively low solubility in water, cannot be transformed to polymer latex by emulsion polymerization because they cannot diffuse through the aqueous phase in order to supply the monomer to the loci of the polymerization.

To solve the foregoing problem, an inert organic solvent has been used to dissolve the UV absorbing monomer and the solution was added to the polymerization vessel containing water, surfactant, and initiator to start the polymerization. This method have been described in EP 0 190 003, U.S. Pat. Nos. 3,761,272, 3,813,255, 4,431,726, 4,455,368, and 4,645,735. Although polymer latexes can be prepared by this method, there are many disadvantages. First, the inert solvent usually must be removed by distillation or diafiltration after the polymerization. This increases the manufacturing cost and adds a waste stream to the process. Second, the inert solvent interferes with the function of surfactants used in emulsion polymerization and reduces the colloidal stability of the polymer latex. Latex then may coagulate during the polymerization or coagulate upon storage. Third, the % solid of the polymer latex is low because it is limited by the solubility of the UV absorbing monomer. Additionally, the use of surfactant for the stabilization of polymer latex have some undesirable effects on the photographic materials. First, some surfactants interact strongly with gelatin and cause coating difficulty. Second, some surfactants have adverse effects on the photographic materials, such as yellowing or stain.

The second way of forming a UV polymer latex is by dispersing polymeric UV absorber made by solution polymerization in an aqueous medium. In this method, all of the ethylenically unsaturated monomers, including UV monomers and comonomer, are dissolved in an organic solvent and an free radical initiator is added to initiate the polymerization (see Billmeyer, Jr., *Textbook of Polymer Science*, Wiley-Interscience (1971). The polymer obtained is isolated by precipitation, redissolved in an auxiliary solvent (i.e. ethyl acetate) and a high-boiling coupler solvent, and subsequently dispersed in aqueous solution containing gelatin and surfactant to form a latex.

The disadvantages of the foregoing method is that the auxiliary solvent used in the dispersion must be removed either by evaporation or washing after the dispersion is made. The dispersion procedure is energy consuming and the dispersion formed needs to be stored in cold condition to prevent aggregation. The particle size of the dispersion made from this process is usually greater than 0.2 μm which tends to increase light scattering in a photographic element and reduce the sharpness of the image which can be produced. Additionally, the use of high boiling permanent solvent for the dispersion tends to damage the physical properties of the photographic materials, such as dry and wet scratch resistance and mushiness. Polymeric UV absorbers prepared by this method have been described in U.S. Pat. Nos. 4,496, 650, 4,431,726, 4,464,462 and 4,645,735.

It would be desirable then, to have a method of making photographic polymeric UV absorbing compounds, and photographic elements containing them, which improves over one or more of the foregoing disadvantages of the known polymerization methods for forming polymeric UV absorbing compounds.

SUMMARY OF THE INVENTION

Accordingly, the present invention provides a photographic element containing a polymeric UV absorbing compound, which compound comprises UV absorbing monomeric units and at least 0.05 weight percent of ionic units which have an ionizable group which is ionized at all pH values between 5 to 10.

The present invention further provides a method of preparing a photographic element of the foregoing type, the method comprising directly dispersing the polymeric UV absorbing compound in water to form a latex, and combining the latex with a binder composition and coating the composition to form a layer of the photographic element. The method can optionally additionally comprise first preparing the polymer by polymerizing a mixture of at least one ethylenically unsaturated UV absorbing monomer and at least one ionic monomer containing an ionizable group that is ionized at all pH between 5 to 10.

The present invention further provides polymeric UV absorbering compounds of the foregoing type.

The polymeric UV absorbers are easily dispersed for use in compositions used for photographic elements, without the use of surfactants or protective colloids such as gelatin, polyvinyl alcohol, and the like. Further the polymeric UV absorbers made by the method of the present invention can use monomers of relatively high melting point and low water solubility. The polymeric UV absorbers prepared by the method of the present invention can also either be dispersed directly in water or isolated as a solid which can be conveniently stored and shipped, and subsequently redispersed in water.

EMBODIMENTS OF THE INVENTION

In the present application, by reference to "under", "above", "below", "upper", "lower" or the like terms in relation to layer structure of a photographic element, is meant in this application, the relative position in relation to light to when the element is exposed in a normal manner. "Above" or "upper" would mean closer to the light source when the element is exposed normally, while "below" or "lower" would mean further from the light source. Since a typical photographic element has the various layers coated on a support, "above" or "upper" would mean further from the support, while "below" or "under" would mean closer to the support. By a "latex" is meant a dispersion of polymer particles in a liquid, gel or the like.

Reference to "directly dispersing in water" or similar terms, in the present application, indicates that the polymer is dispersed in water without the use of surfactants or emulsifiers. It will be understood, of course, that this includes the polymer composition being added to water or water being added to the polymer composition. In reference to "polymers" having units formed from UV absorbing monomers, this means that the compound would contain at least 10 (and preferably at least 20 and more preferably at least 50) units of a UV absorbing monomer (usually at least the foregoing numbers of the same units). Typically the polymers would have hundreds (for example, three hundred or more) or several thousand (for example, three thousand or more) units of UV absorbing monomers (usually at least the foregoing numbers of the same units). For a compound to be considered a UV absorbing one in the present invention, within the range of 300 to 800 nm it should a wavelength of maximum absorbance between 300 to 400 nm with a minimum extinction coefficient of 5,000. Preferably it also has no substantial absorption above 400 nm. Particularly it should have a maximum absorbance in the range of 330–380 nm. When reference in this application is made to a substituent "group", this means that the substituent may itself be substituted or unsubstituted (for example "alkyl group" refers to a substituted or unsubstituted alkyl). Generally, unless otherwise specifically stated, substituents on any "groups" referenced herein or where something is stated to be possibly substituted, include the possibility of any groups, whether substituted or unsubstituted, which do not destroy properties necessary for the photographic utility. It will also be understood throughout this application that reference to a compound of a particular general formula includes those compounds of other more specific formula which specific formula falls within the general formula definition. Examples of substituents on any of the mentioned groups can include known substituents, such as: halogen, for example, chloro, fluoro, bromo, iodo; alkoxy, particularly those with 1 to 6 carbon atoms (for example, methoxy, ethoxy); substituted or unsubstituted alkyl, particularly lower alkyl (for example, methyl, trifluoromethyl); alkenyl or thioalkyl (for example, methylthio or ethylthio), particularly either of those with 1 to 6 carbon atoms; substituted and unsubstituted aryl, particularly those having from 6 to 20 carbon atoms (for example, phenyl); and substituted or unsubstituted heteroaryl, particularly those having a 5 or 6-membered ring containing 1 to 3 heteroatoms selected from N, O, or S (for example, pyridyl, thienyl, furyl, pyrrolyl); and others known in the art. Alkyl substituents may specifically include "lower alkyl", that is having from 1 to 6 carbon atoms, for example, methyl, ethyl, and the like. Further, with regard to any alkyl group, alkylene group or alkenyl group, it will be understood that these can be branched or unbranched and include ring structures.

As to the ionizable group on the ionic units, such group preferably is ionized at all pH values between 2 to 14 (although this could optionally be extended to 1 to 14), although less preferably it could be ionized only at pH 5–10. By the group being ionized in this context is meant that under equilibrium conditions in water, at any values within the recited pH range, at least 90 mole % (and preferably greater than 95 mole %) would be ionized. Preferable ionizable groups include sulfonate, sulfate, sulfinate. Phosphate and carboxylic acid can also be used but is less preferred. Particularly, the ionizable groups could optionally exclude carboxylic acid.

The UV absorbing polymer can contain any amount (but particularly at least 0.05 weight %) of the described ionic units. However, the maximum amount of the ionic units may be limited to up to 20 weight % (although this could be limited to 10%). Above 20 weight percent, the polymer may become water soluble and may cause adverse effects such as high coating viscosity or even wash out from the photographic element during processing. Preferably, the ionic units are present in an amount of from 1 to 5 weight % of the polymer. The photographic elements of the present invention typically have the UV absorbing polymer present as a latex dispersion, typically in a binder. Most typically, the binder is a gelatin containing composition. Unlike latexes prepared by emulsion polymerization, the UV polymer of this invention, when directly dispersed in an water, can form non-spherical particles.

As to the UV absorbing units in the UV absorbing polymer, these can, for example, be units which contain a phenyl substituted triazole (such as 2-hydroxyphenylbenzotriazole) or a phenyl substituted triazine (it being understood that when any particular unit of a polymer is referenced, that can be obtained by polymerization using the corresponding monomer). However, many other UV absorbing ethylenically unsaturated monomers can be used to provide corresponding UV absorbing units in the polymer. In particular, such other monomers and monomeric units formed from them are described, for example, in U.S. Pat. Nos. 4,716,234, 4,528,311, 4,4496,650, EP 0 190 003, U.S. Pat. Nos. 4,785,063, 3,072,585, 3,493,539, 3,761,272, 3,813,255, 3,980,617, 4,166,109, 4,307,184, 4,276,401, 4,380,643, 4,464,462, 4,431,726, 4,645,735, 4,455,368, 4,496,650, 4,528,311, 4,611,061, 4,716,234, 4,663,272, 4,652,656, 4,686,268, 4,785,063, JP 63 55542, U.S. Pat. Nos. 4,845,180, 4,892,915, EP 474 595, U.S. Pat. Nos. 5,099,027, 5,133,745, and allowed U.S. patent application Ser. No. 07/907,008 by Chen et al. (filed Jul. 1, 1992). The foregoing references, and every other reference cited in this application, are incorporated herein by reference. In particular, the general and specific formulae of the ethylenically unsaturated UV absorbing monomers and monomeric units in the foregoing patents and patent publications, are particularly incorporated herein by reference.

Particularly suitable UV absorbing monomers are represented by the following general formula (I):

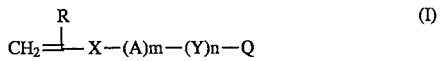

(I)

wherein R represents a hydrogen atom, a lower alkyl group having from 1 to 4 carbon atoms(for example, a methyl group, an ethyl group, an n-propyl group, an isopropyl group, etc.) or a chlorine atom; X represents —CONH—, —COO—, or a phenylene group; A represents a linking group selected from an alkylene group having from 1 to 20 carbon atoms (for example, a methylene group, an ethylene group, a trimethylene group, a 2-hydroxytrimethylene group, a pentamethylene group, etc.) or an arylene group having from 6 to 20 carbon atoms (for example, a phenylene group, etc.); Y represents —COO—, —OCO—, —CONH—, —NHCO—, $SO_2NH$—, $NHSO_2$—, —$SO_2$—, or —O—; m represents 0 or an integer of 1; n represents 0 or an integer of 1; and Q represents an UV absorbing group represented by any of the following general formula (II) to (XI) in which —' represents the point of attachment to the remainder of formula (I):

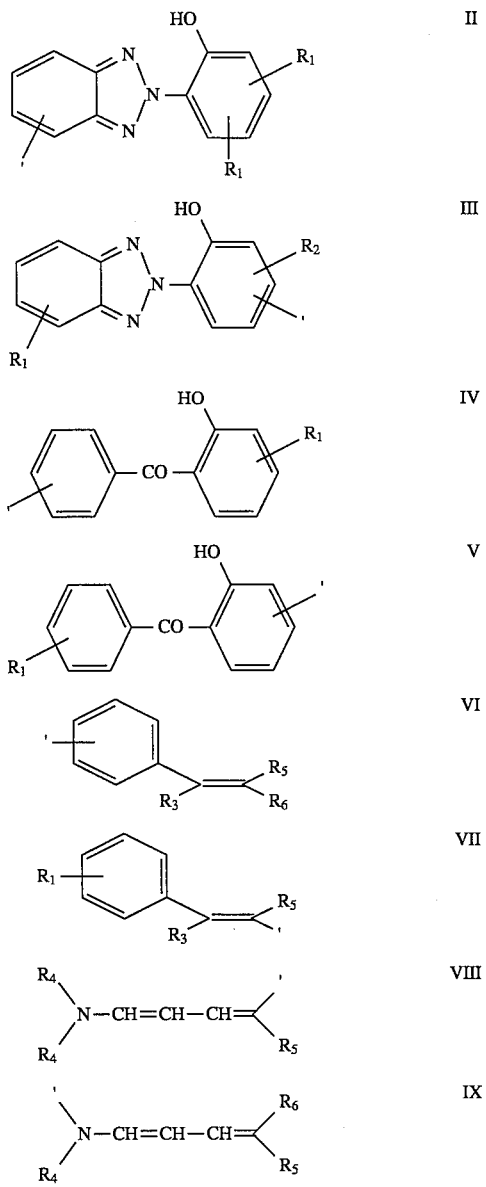

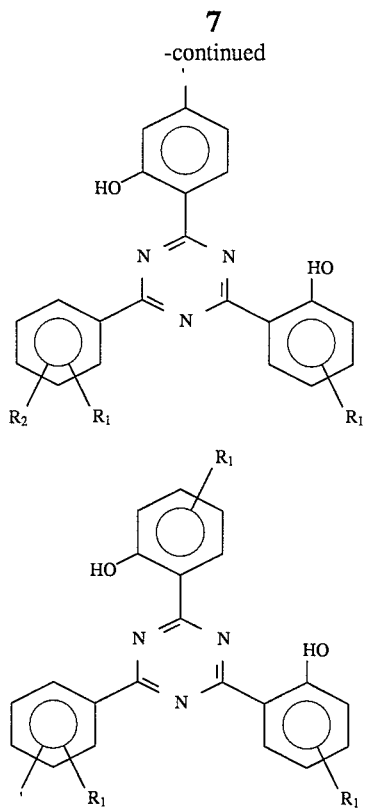

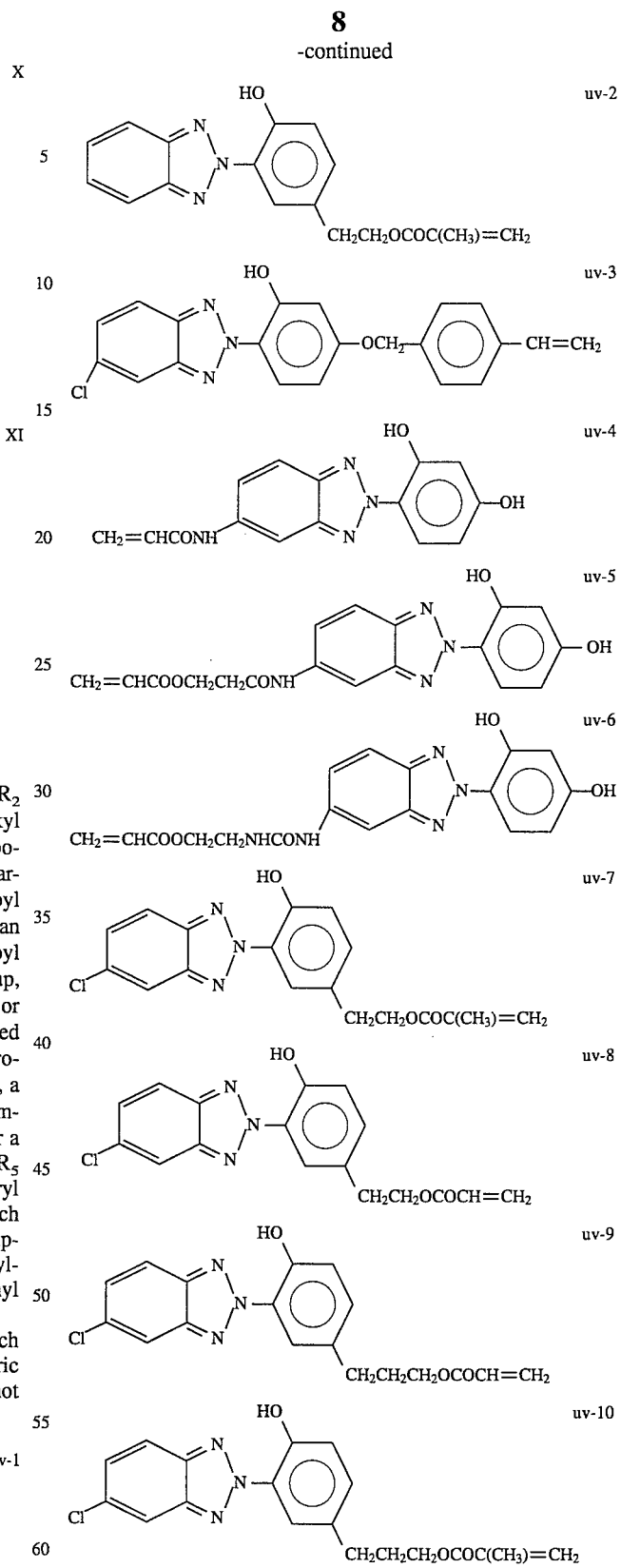

In the above UV absorbing group structures, $R_1$ and $R_2$ each independently represents a hydrogen atom, an alkyl group, an alkenyl group, an alkoxy group, an alkoxycarbonyl group, a halogen atom, a hydroxy group, an alkoxycarbamoyl group, an aliphatic amido group, an alkylsulfamoyl group, an alkylsulfonamido group, an alkylureido group, an arylcarbamoyl group, an arylamido group, an arylsulfamoyl group, an arylsulfonamido group, an arylureido group, caboxyl group, sulfo group, nitro group, cyano group, or thiocyano group. $R_3$ represents an aryl group, a substituted aryl group or a hetereocyclic group. $R_4$ represents a hydrogen atom, an alkyl group containing 1 to 4 carbon atoms, a hydroxyalkyl group containing from 1 to 4 carbon atoms(such as hydoxymethyl group or hydroxyethyl group) or a sulfoalkyl group containing from 1 to 4 carbon atoms. $R_5$ and $R_6$ each independently represents a cyano group, an aryl group( such as phenyl or tolyl group), an alkyl group(such as methyl, ethyl, butyl, or hexyl), an alkoxycarbonyl group-(such as ethoxycarbonyl or propoxycarbonyl), an arylsulfonyl group (such as phenylsulfonyl), or an alkylsulfonyl group (such as methylsulfulonyl).

Preferred ethylenically unsaturated UV monomers which may be used in preparing the water-dispersible polymeric UV absorbers of the present invention include, but are not limited to, the following monomers:

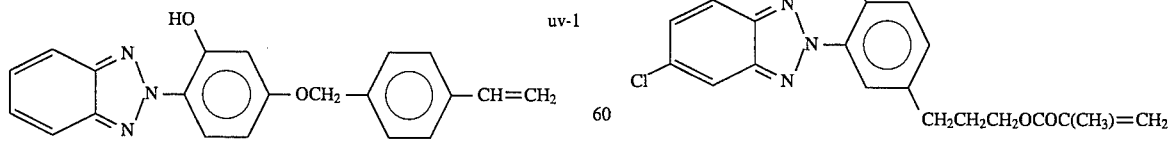

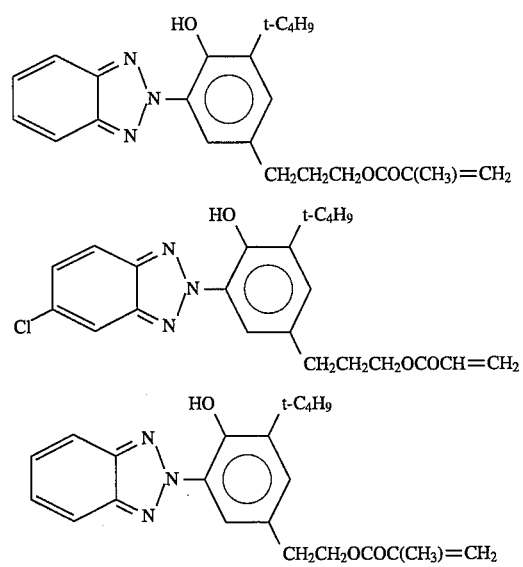

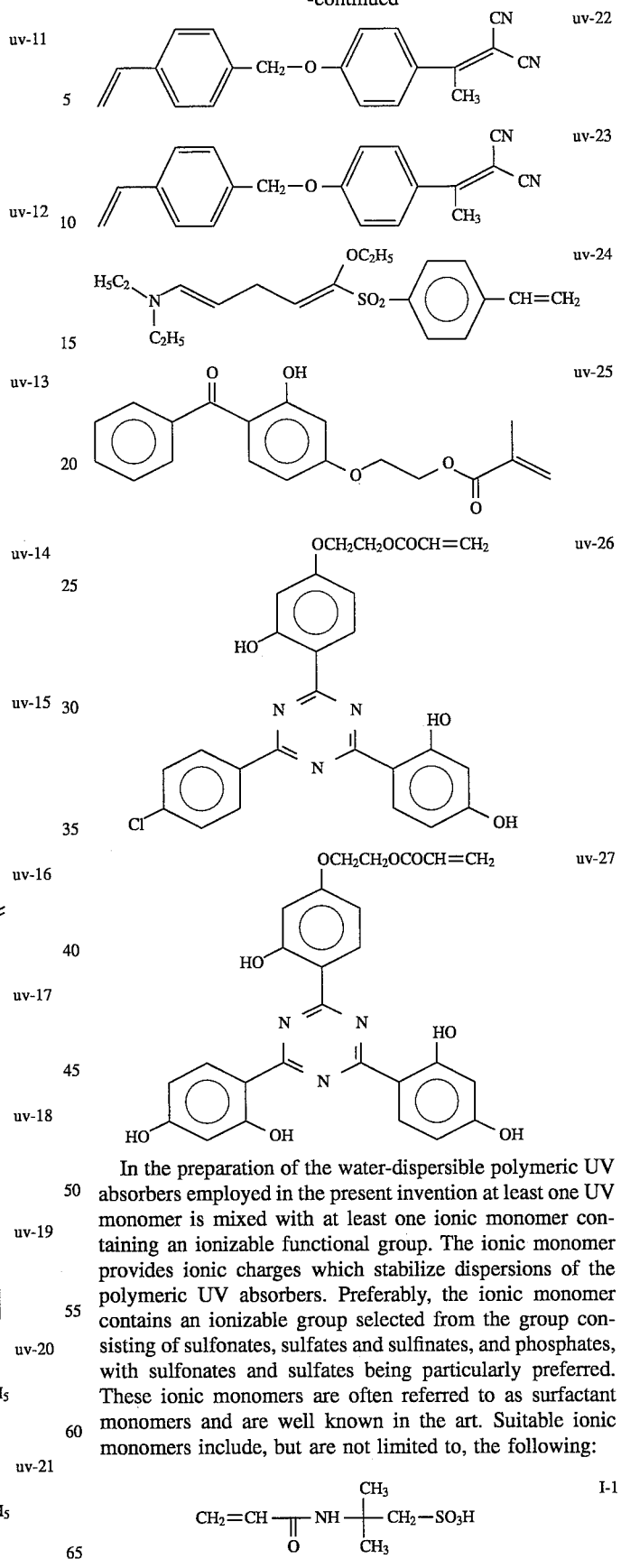

In the preparation of the water-dispersible polymeric UV absorbers employed in the present invention at least one UV monomer is mixed with at least one ionic monomer containing an ionizable functional group. The ionic monomer provides ionic charges which stabilize dispersions of the polymeric UV absorbers. Preferably, the ionic monomer contains an ionizable group selected from the group consisting of sulfonates, sulfates and sulfinates, and phosphates, with sulfonates and sulfates being particularly preferred. These ionic monomers are often referred to as surfactant monomers and are well known in the art. Suitable ionic monomers include, but are not limited to, the following:

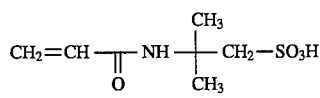

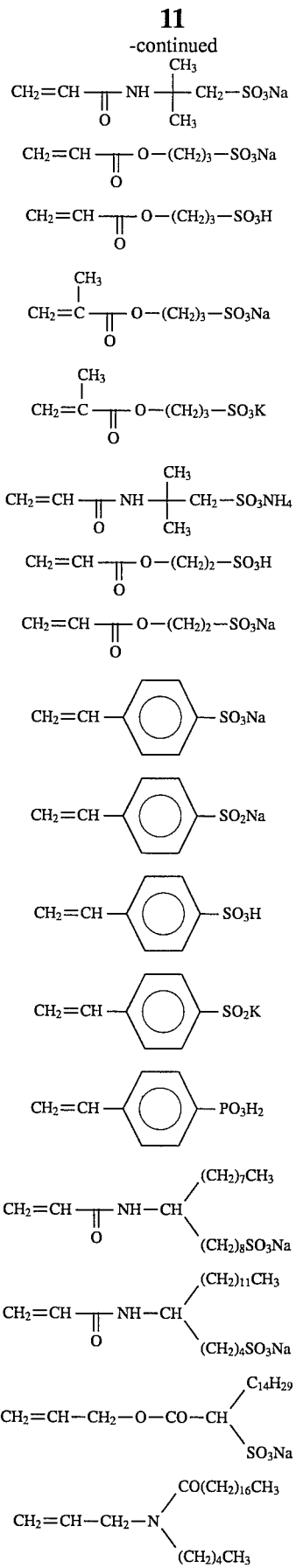

I-2

I-3

I-4

I-5

I-6

I-7

I-8

I-9

I-10

I-11

I-12

I-13

I-14

I-15

I-16

I-17

I-18

$CH_2=CH-SO_3Na$   I-19

The ionic monomer is included in the polymerization mixture in an amount sufficient to provide the polymeric UV absorber with preferably less than 20 weight percent of the ionic monomer, and, preferably, with from 1 to 5 weight percent of the ionic monomers. The mixture from which the polymeric UV absorber is polymerized may further include at least one additional non-UV-absorbing ethylenically unsaturated monomer. The non-UV-absorbing monomer may be selected so as to provide useful physical and chemical properties for the polymeric UV absorber, including useful solubility, compatibility with other components of the photographic materials, glass transition temperature, amphiphilic properties, and particle size of the polymer particles.

Examples of the non-UV-absorbing diluent monomers (comonomers) used for copolymerizing with the UV absorbing monomers include an acrylic acid, an a-alkylacrylic acid (such as methacrylic acid, etc.), an ester or amide derived from an acrylic acid(for example, acrylamide, methacrylamide, hydroxymethylacrylamide, t-butylacrylamide, acrn-butylacrylamide, t-butylacrylamide, diacetone acrylamide, methyl acrylate, ethyl acrylate, n-propylacrylate, n-butyl acrylate, t-butyl acrylate, isobutyl acrylate, 2-ethylhexyl acrylate, n-octyl acrylate, lauryl acrylate, 2-ethoxyethyl acrylate, 2-methoxyethyl acrylate, methyl methacrylate, ethyl methacrylate, n-butyl methacrylate, b-hydroxyl methacrylate, etc.), a vinyl ester(for example, vinyl acetate, vinyl propionate, vinyl laurate, etc.), acrylonitrile, methacrylonitrile, an aromatic vinyl compound (for example, styrene and a derivative thereof, for example, vinyl toluene, divinylbenzene, vinyl acetophenone, sulfostyrene, etc.), itaconic acid, citraconic acid, crotonic acid, vinylidene chloride, a vinyl alkyl ether (for example, vinyl ethyl ether, etc.), an ester of maleic acid, N-vinyl-2-pyrrolidone, N-vinylpyridine, 2- or 4-vinylpyridine, etc., an sulfonic acid containing monomers, (for example, acrylamido-2,2'-dimethyl-propane sulfonic acid, 2-sulfoethyl methacrylate, 3-sulfopropyl methacylate, etc.). Of these monomers, an amide of acrylic acid, an ester of acrylic acid, an ester of methacrylic acid, and an aromatic vinyl compounds are particularly preferred.

The UV absorbing polymer of the present invention is preferably prepared by solution polymerization in an organic solvent including, but not limited to, methanol, ethanol, propanol, isopropanol, dimethylsulfoxide, dimethylacetamide, N,N-dimethylformamide, dioxane, acetone, methylethyl ketone, tetrahydrofuran, N-methyl pyrrolidone, ethylene glycol, diethylene glycol, triethylene glycol, and the like. Conventional solution polymerization techniques are employed, either semicontinuously or batchwise. Solution polymerization is well known in the art and described, for example, in *Polymer Synthesis, S. R. Sandler and W. Karo, Academic Press, Inc., New York, p.285* (1974). Preferred initiators for use in the solution polymerization process are the azo type and peroxy type initiators, such as 2,2,-azobis(2-methylpropionitrile, 2,2-azobisisobutylonitrile, 2,2azobis(-2,4-dimethyl-valeronitrile), 2,2-azobs(2-amidinopropane)dihydrochloride, 4,4-azobis(4-cyanopentanoic acid), hydrogen peroxide, t-butylperoxide, benzophenone, benzoyl peroxide, isobutyroyl peroxide, acetyl peroxide, propionyl peroxide, and the like. The amount of initiator is adjusted in accordance with the molecular weight of the polymer to be produced, and it is preferably in the range of about 0.001 to 50 mol percent, more preferably 0.01 to 10 mol percent, of the monomer.

The mixture of monomers which is polymerized to form the polymeric UV absorber of the present invention includes the ionic monomer in an amount sufficient to provide the polymeric UV absorber with less than 20 weight percent of the ionic monomer. Preferably, the ionic monomer is included in an amount sufficient to provide the polymeric absorber with from 1 to 10 or even more preferably, 1 to 5, weight percent of the ionic monomer. In a further preferred embodiment, the polymeric UV absorber contains from 10 to 90 percent by weight of the UV absorbing monomer, more preferably from 30 to 70 percent by weight of the UV monomer, not greater than 20 percent by weight of the ionic monomer and a remainder of one or more non-UV-absorbing monomers. The average particle size of the water-dispersed polymeric UV absorber according to the present invention is generally in a range of from about 20 to 250 nanometers, depending on the amount of ionic monomer included therein. Additionally, the polymeric UV absorbers preferably have a weight average molecular weight of 2,000 to 50,000.

The polymeric UV absorber is incorporated into the color photographic materials in the form of a latex in water. The water-dispersed polymeric UV absorber may be formed according to several methods. That is, the polymer product resulting from the solution polymerization may optionally be diluted with a water-miscible organic solvent and then directly dispersed into water. Alternatively, water may be added to an organic solvent diluted solution product as prepared above to produce a stable polymer dispersion in water by phase inversion. The polymer product resulting from the solution polymerization may also be isolated as a solid and then later added to a water-miscible organic solvent and redispersed in water as described above (that is, directly dispersed in water), or in some cases where there is sufficient ionic monomer present the polymer can be redispersed in water without the aid of organic solvent. In either case, no surfactant, or emulsifiers or protective colloids are necessary although any of them can be used if desired.

Thus, the polymeric UV absorber of the present invention is advantageous in that it may be isolated as a solid, for example, to facilitate storage and shipping, and then easily dispersed in water at a later time as already described. Preferably, the water which is added to the polymer product or to which the polymer product is added has a volume of 0.5 to 20 times, and more preferably at least equal to, that of the diluted polymer product or optionally-diluted polymer product. To facilitate dispersion, the water may be heated, for example, to a temperature of from 20° to 100° C. Additionally, when the polymer product is diluted with an organic solvent as described above, it is preferred that the polymer product is diluted to a concentration of not greater than 50 weight percent, and more preferably 30 weight percent, polymer product.

Two or more of the UV absorbing monomers can be copolymerized together, for example, a combination of UV-1 with UV-6 or with other UV absorbing monomers described in the prior art. The conventional UV absorbing agents can be loaded into these polymeric UV absorbing agent to alter its photographic performance. Examples of the conventional UV absorbing agents can be used include 2-(2-hydroxy-5-methylphenyl)-2H-benzotriazole, 2-(2-hydroxy-3,5-di-tert-butylphenyl)-2H-benzotriazole, 2-(2-hydroxy-3-tert-butyl-5-methylphenyl)-2H-benzotriazole, 2-(2-hydroxy-3,5-di-tert-butylphenyl)-5-chloro-2H-benzotriazole, 2-(2-hydroxy-3,5-di-tert-amylphenyl)-2H-benzotriazole, 2-(2-hydroxy-3,5-di(1,1-dimethylbenzyl)-phenyl)-2H-benzotriazole, 2-(2-hydroxy-5-tert-octylphenyl)-2H-benzotriazole, and other types of UV absorbing agents such as p-hydroxybenzoates, phenylesters of benzoic acid, salicylanilides and oxanilides, diketones, benzylidene malonate, esters of 1-cyano-b-phenylcinnamic acid, and organic metal photostabilizers, etc. as described in J. F. Rabek, *Photostabilization of Polymers, Principles and Applications*, Elsevier Science Publishers LTD, page 202–278(1990).

The high boiling organic solvents can also be loaded into these polymeric UV absorbing agents to alter its photographic performance. Examples of such high-boiling organic solvents include tricresyl phosphate, di-n-butyl phthalate, N-n-amylphthalimide, bis(2-methoxyethyl)phthalate, dimethyl phthalate, ethyl N,N-di-n-butyl-carbamate, diethyl phthalate, n-butyl 2-methoxybenzoate, 2-(n-butoxyethyl) phthalate, ethyl benzylmalonate, n-amyl phthalate, n-hexyl benzoate, guaiacol acetate, tri-m-cresyl phosphate, diethyl sebacate, di-isoamyl phthalate, ethyl phenylacetate, phorone, di-n-butyl sebacate, dimethyl sebacate, N,N-diethyl lauramide, N,N-di-n-butyl lauramide, phenethyl benzoate, benzyl benzoate, dioctyl phthalate, dioctyl sebacate, quinitol bis(2-ethylhexoate), cresyl diphenyl phosphate, butyl cyclohexyl phthalate, tetrahydrofurfuryl adipate, tetrahydrofurfuryl benzoate, tetrahydrofurfuryl propionate, tetrahydrofurfuryl palmitate, quaiacol n-caproate, bis(tetrahydrofurfuryl)phthalate, N,N-diethylcapramide, 2,4-di-tert-amylphenol, 1-lauryl piperidine, N-n-butylacetanilide, N,N, N',N'-tetraethyl phthalamide, N,n-amylsuccinimide, diethyl citrate, 2,4-di-n-amylphenol, 1,4-cyclohexyllemedimethylene bis(2-ethylhexanoate), benzylbutyl phthalate, p-dodecylphenol, trihexylphosphate, isopropyl plamitate, and bis(2-ethylhexyl)sulfoxide, etc.

The loading of high boiling organic solvents into a polymer latex is described in the following publications: U.S. Pat. Nos. 4,199,363, 4,203,716, 4,214,047, 4,247,627, 4,497,929, and 4,608,424.

The UV absorbing polymer dispersion is incorporated into the photographic element (typically into a gelatin gel thereof) in an amount of between 0.2 g/m$^2$ to 10 g/m$^2$, and more preferably between 0.5 g/m$^2$ to 5.0 g/m$^2$. Furthermore, the weight ratio of high boiling, water immiscible organic solvent, if present at all, can particularly be between 0.1 to 5.0 (that is, 0.1/1 to 5.0/1 of solvent/polymer latex), and more preferably between 0.2 to 3.0 (that is, 0.2/1 to 3.0/1 of solvent/polymer latex).

Photographic elements according to the present invention will typically have at least one light sensitive silver halide emulsion layer and a non-light sensitive layer, with the ultraviolet absorbing polymer of the present invention being typically (but not necessarily) located in the non-light sensitive layer. More preferably, a photographic element of the present invention will have the non-light sensitive layer containing the ultraviolet absorbing polymer located above all light sensitive layers. However, it is also contemplated that the ultraviolet absorbing polymer can additionally be present in another layer, such as an interlayer (or even a light sensitive layer), particularly an interlayer located between red and green sensitive layers in an element having blue, green and red-sensitive layers coated in that order, on a support (particularly a paper support). Any layer of the photographic element in which the UV absorbing polymer compounds of the present invention are located, will normally be a gel layer, and the UV absorbing compound may particularly be dispersed therein using a coupler solvent with or without additional ethyl acetate.

The UV absorbing polymers of the present invention is provided in any one or more of the layers (for example, a hydrophilic colloid layer such as a gelatin layer) of a photographic light-sensitive material (for example, a silver halide photographic light-sensitive material), such as a surface protective layer, an intermediate layer or a silver halide emulsion layer, and the like. For example, in photographic paper the UV absorbing polymer of the present invention with/without other UV absorbing compounds, may be positioned above and/or below the red sensitive layer (typically adjacent to it), the red sensitive layer typically being the uppermost light sensitive layer in color paper, or even completely or partially within the red sensitive layer. The UV absorbing compound is typically provided in a given layer of a photographic element by coating the hydrophilic colloid material (such as a gelatin emulsion) which contains the latex, onto a support or another previously coated layer forming part of the element.

The photographic elements made by the method of the present invention can be single color elements or multicolor elements. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye-forming coupler, and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like. All of these can be coated on a support which can be transparent or reflective (for example, a paper support). Photographic elements of the present invention may also usefully include a magnetic recording material as described in Research Disclosure, Item 34390, November 1992, or a transparent magnetic recording layer such as a layer containing magnetic particles on the underside of a transparent support as in U.S. Pat. Nos. 4,279,945 and 4,302,523. The element typically will have a total thickness (excluding the support) of from 5 to 30 microns. While the order of the color sensitive layers can be varied, they will normally be red-sensitive, green-sensitive and blue-sensitive, in that order on a transparent support, (that is, blue sensitive furthest from the support) and the reverse order on a reflective support being typical.

The present invention also contemplates the use of photographic elements of the present invention in what are often referred to as single use cameras (or "film with lens" units). These cameras are sold with film preloaded in them and the entire camera is returned to a processor with the exposed film remaining inside the camera. Such cameras may have glass or plastic lenses through which the photographic element is exposed.

In the following discussion of suitable materials for use in elements of this invention, reference will be made to *Research Disclosure*, September 1994, Number 365, Item 36544, published by Kenneth Mason Publications, Ltd., Dudley Annex, 12a North Street, Emsworth, Hampshire P010 7DQ, ENGLAND, which will be identified hereafter by the term "Research Disclosure I." The Sections hereafter referred to are Sections of the Research Disclosure I.

The silver halide emulsions employed in the elements of this invention can be either negative-working, such as surface-sensitive emulsions or unfogged internal latent image forming emulsions, or direct positive emulsions of the unfogged, internal latent image forming type which are positive working when development is conducted with uniform light exposure or in the presence of a nucleating agent. Suitable emulsions and their preparation as well as methods of chemical and spectral sensitization are described in Sections I through V. Color materials and development modifiers are described in Sections V through XX. Vehicles which can be used in the elements of the present invention are described in Section II, and various additives such as brighteners, antifoggants, stabilizers, light absorbing and scattering materials, hardeners, coating aids, plasticizers, lubricants and matting agents are described, for example, in Sections VI through X and XI through XIV. Manufacturing methods are described in all of the sections, other layers and supports in Sections XI and XIV, processing methods and agents in Sections XIX and XX, and exposure alternatives in Section XVI.

With negative working silver halide a negative image can be formed. Optionally a positive (or reversal) image can be formed although a negative image is typically first formed.

The photographic elements of the present invention may also use colored couplers (e.g. to adjust levels of interlayer correction) and masking couplers such as those described in EP 213 490; Japanese Published Application 58-172,647; U.S. Pat. No. 2,983,608; German Application DE 2,706, 117C; U.K. Patent 1,530,272; Japanese Application A-113935; U.S. Pat. No. 4,070,191 and German Application DE 2,643,965. The masking couplers may be shifted or blocked.

The photographic elements may also contain materials that accelerate or otherwise modify the processing steps of bleaching or fixing to improve the quality of the image. Bleach accelerators described in EP 193 389; EP 301 477; U.S. Pat. Nos. 4,163,669; 4,865,956; and 4,923,784 are particularly useful. Also contemplated is the use of nucleating agents, development accelerators or their precursors (UK Patent 2,097,140; U.K. Patent 2,131,188); electron transfer agents (U.S. Pat. Nos. 4,859,578; 4,912,025); anti-fogging and anti color-mixing agents such as derivatives of hydroquinones, aminophenols, amines, gallic acid; catechol; ascorbic acid; hydrazides; sulfonamidophenols; and non color-forming couplers.

The elements may also contain filter dye layers comprising colloidal silver sol or yellow and/or magenta filter dyes and/or antihalation dyes (particularly in an undercoat beneath all light sensitive layers or in the side of the support opposite that on which all light sensitive layers are located) either as oil-in-water dispersions, latex dispersions or as solid particle dispersions. Additionally, they may be used with "smearing" couplers (e.g. as described in U.S. Pat. No. 4,366,237; EP 096 570; U.S. Pat. No. 4,420,556; and U.S. Pat. No. 4,543,323.) Also, the couplers may be blocked or coated in protected form as described, for example, in Japanese Application 61/258,249 or U.S. Pat. No. 5,019, 492.

The photographic elements may further contain other image-modifying compounds such as "Developer Inhibitor-Releasing" compounds (DIR's). Useful additional DIR's for elements of the present invention, are known in the art and examples are described in U.S. Pat. Nos. 3,137,578; 3,148, 022; 3,148,062; 3,227,554; 3,384,657; 3,379,529; 3,615, 506; 3,617,291; 3,620,746; 3,701,783; 3,733,201; 4,049, 455; 4,095,984; 4,126,459; 4,149,886; 4,150,228; 4,211, 562; 4,248,962; 4,259,437; 4,362,878; 4,409,323; 4,477, 563; 4,782,012; 4,962,018; 4,500,634; 4,579,816; 4,607, 004; 4,618,571; 4,678,739; 4,746,600; 4,746,601; 4,791, 049; 4,857,447; 4,865,959; 4,880,342; 4,886,736; 4,937, 179; 4,946,767; 4,948,716; 4,952,485; 4,956,269; 4,959, 299; 4,966,835; 4,985,336 as well as in patent publications GB 1,560,240; GB 2,007,662; GB 2,032,914; GB 2,099, 167; DE 2,842,063, DE 2,937,127; DE 3,636,824; DE 3,644,416 as well as the following European Patent Publications: 272,573; 335,319; 336,411; 346, 899; 362, 870; 365,252; 365,346; 373,382; 376,212; 377,463; 378,236; 384,670; 396,486; 401,612; 401,613.

DIR compounds are also disclosed in "Developer-Inhibitor-Releasing (DIR) Couplers for Color Photography," C. R. Barr, J. R. Thirtle and P. W. Vittum in *Photographic Science and Engineering*, Vol. 13, p. 174 (1969), incorporated herein by reference.

It is also contemplated that the concepts of the present invention may be employed to obtain reflection color prints as described in *Research Disclosure*, November 1979, Item 18716, available from Kenneth Mason Publications, Ltd, Dudley Annex, 12a North Street, Emsworth, Hampshire P0101 7DQ, England, incorporated herein by reference. The emulsions and materials to form elements of the present invention, may be coated on pH adjusted support as described in U.S. Pat. No. 4,917,994; with epoxy solvents (EP 0 164 961); with additional stabilizers (as described, for example, in U.S. Pat. Nos. 4,346,165; 4,540,653 and 4,906, 559); with ballasted chelating agent s such as those in U.S. Pat. No. 4,994,359 to reduce sensitivity to polyvalent cations such as calcium; and with stain reducing compounds such as described in U.S. Pat. No. 5,068,171 and U.S. Pat. No. 5,096,805. Other compounds useful in the elements of the invention are disclosed in Japanese Published Applications 83-09,959; 83-62,586; 90-072,629, 90-072,630; 90-072, 632; 90-072,633; 90-072,634; 90-077,822; 90-078,229; 90-078,230; 90-079,336; 90-079,338; 90-079,690; 90-079, 691; 90-080,487; 90-080,489; 90-080,490; 90-080,491; 90-080,492; 90-080,494; 90-085,928; 90-086,669; 90-086, 670; 90-087,361; 90-087,362; 90-087,363; 90-087,364; 90-088,096; 90-088,097; 90-093,662; 90-093,663; 90-093, 664; 90-093,665; 90-093,666; 90-093,668; 90-094,055; 90-094,056; 90-101,937; 90-103,409; 90-151,577.

The silver halide used in the photographic elements of the present invention may be silver iodobromide, silver bromide, silver chloride, silver chlorobromide, silver chloroiodobromide, and the like. The type of silver halide grains preferably include polymorphic, cubic, and octahedral. The grain size of the silver halide may have any distribution known to be useful in photographic compositions, and may be ether polydipersed or monodispersed. Particularly useful in this invention are tabular grain silver halide emulsions. Specifically contemplated tabular grain emulsions are those in which greater than 50 percent of the total projected area of the emulsion grains are accounted for by tabular grains having a thickness of less than 0.3 micron (0.5 micron for blue sensitive emulsion) and an average tabularity (T) of greater than 25 (preferably greater than 100), where the term "tabularity" is employed in its art recognized usage as $$T = ECD/t^2$$

where

ECD is the average equivalent circular diameter of the tabular grains in microns and t is the average thickness in microns of the tabular grains.

The average useful ECD of photographic emulsions can range up to about 10 microns, although in practice emulsion ECD's seldom exceed about 4 microns. Since both photographic speed and granularity increase with increasing ECD's, it is generally preferred to employ the smallest tabular grain ECD's compatible with achieving aim speed requirements.

Emulsion tabularity increases markedly with reductions in tabular grain thickness. It is generally preferred that aim tabular grain projected areas be satisfied by thin (t<0.2 micron) tabular grains. To achieve the lowest levels of granularity it is preferred to that aim tabular grain projected areas be satisfied with ultrathin (t<0.06 micron) tabular grains. Tabular grain thicknesses typically range down to about 0.02 micron. However, still lower tabular grain thicknesses are contemplated. For example, Daubendiek et al U.S. Pat. No. 4,672,027 reports a 3 mole percent iodide tabular grain silver bromoiodide emulsion having a grain thickness of 0.017 micron.

As noted above tabular grains of less than the specified thickness account for at least 50 percent of the total grain projected area of the emulsion. To maximize the advantages of high tabularity it is generally preferred that tabular grains satisfying the stated thickness criterion account for the highest conveniently attainable percentage of the total grain projected area of the emulsion. For example, in preferred emulsions tabular grains satisfying the stated thickness criteria above account for at least 70 percent of the total grain projected area. In the highest performance tabular grain emulsions tabular grains satisfying the thickness criteria above account for at least 90 percent of total grain projected area.

Suitable tabular grain emulsions can be selected from among a variety of conventional teachings, such as those of the following:

*Research Disclosure*, Item 22534, January 1983, published by Kenneth Mason Publications, Ltd., Emsworth, Hampshire P010 7DD, England; U.S. Pat. Nos. 4,439,520; 4,414, 310; 4,433,048; 4,643,966; 4,647,528; 4,665,012; 4,672, 027; 4,678,745; 4,693,964; 4,713,320; 4,722,886; 4,755, 456; 4,775,617; 4,797,354; 4,801,522; 4,806,461; 4,835, 095; 4,853,322; 4,914,014; 4,962,015; 4,985,350; 5,061,069 and 5,061,616.

The silver halide grains to be used in the invention may be prepared according to methods known in the art, such as those described in Research Disclosure I and James, The Theory of the Photographic Process. These include methods such as ammoniacal emulsion making, neutral or acidic emulsion making, and others known in the art. These methods generally involve mixing a water soluble silver salt with a water soluble halide salt in the presence of a protective colloid, and controlling the temperature, pAg, pH values, etc, at suitable values during formation of the silver halide by precipitation.

The silver halide to be used in the invention may be advantageously subjected to chemical sensitization with noble metal (for example, gold) sensitizers, middle chalcogen (for example, sulfur) sensitizers, reduction sensitizers and others known in the art. Compounds and techniques useful for chemical sensitization of silver halide are known in the art and described in Research Disclosure I and the references cited therein.

The photographic elements of the present invention, as is typical, provide the silver halide in the form of an emulsion. Photographic emulsions generally include a vehicle for coating the emulsion as a layer of a photographic element.

Useful vehicles include both naturally occurring substances such as proteins, protein derivatives, cellulose derivatives (e.g., cellulose esters), gelatin (e.g., alkali-treated gelatin such as cattle bone or hide gelatin, or acid treated gelatin such as pigskin gelatin), gelatin derivatives (e.g., acetylated gelatin, phthalated gelatin, and the like), and others as described in Research Disclosure I. Also useful as vehicles or vehicle extenders are hydrophilic water-permeable colloids. These include synthetic polymeric peptizers, carriers, and/or binders such as poly(vinyl alcohol), poly(vinyl lactams), acrylamide polymers, polyvinyl acetals, polymers of alkyl and sulfoalkyl acrylates and methacrylates, hydrolyzed polyvinyl acetates, polyamides, polyvinyl pyridine, methacrylamide copolymers, and the like, as described in Research Disclosure I. The vehicle can be present in the emulsion in any amount useful in photographic emulsions. The emulsion can also include any of the addenda known to be useful in photographic emulsions. These include chemical sensitizers, such as active gelatin, sulfur, selenium, tellurium, gold, platinum, palladium, iridium, osmium, rhenium, phosphorous, or combinations thereof. Chemical sensitization is generally carried out at pAg levels of from 5 to 10, pH levels of from 5 to 8, and temperatures of from 30 to 80° C., as illustrated in Research Disclosure, June 1975, item 13452 and U.S. Pat. No. 3,772,031.

The silver halide may be sensitized by sensitizing dyes by any method known in the art, such as described in Research Disclosure I. The dye may be added to an emulsion of the silver halide grains and a hydrophilic colloid at any time prior to (e.g., during or after chemical sensitization) or simultaneous with the coating of the emulsion on a photographic element. The dye/silver halide emulsion may be mixed with a dispersion of color image-forming coupler immediately before coating or in advance of coating (for example, 2 hours).

Photographic elements of the present invention are preferably imagewise exposed using any of the known techniques, including those described in Research Disclosure I, section XVI. This typically involves exposure to light in the visible region of the spectrum, and typically such exposure is of a live image through a lens, although exposure can also be exposure to a stored image (such as a computer stored image) by means of light emitting devices (such as light emitting diodes, CRT and the like).

Photographic elements comprising the composition of the invention can be processed in any of a number of well-known photographic processes utilizing any of a number of well-known processing compositions, described, for example, in Research Disclosure I, or in T. H. James, editor, The Theory of the Photographic Process, 4th Edition, Macmillan, New York, 1977. In the case of processing a negative working element, th element is treated with a color developer (that is one which will form the colored image dyes with the color couplers), and then with a oxidizer and a solvent to remove silver and silver halide. In the case of processing a reversal color element, the element is first treated with a black and white developer (that is, a developer which does not form colored dyes with the coupler compounds) followed by a treatment to fog silver halide (usually chemical fogging or light fogging), followed by treatment with a color developer. Preferred color developing agents are p-phenylenediamines. Especially preferred are:

4-amino N,N-diethylaniline hydrochloride,
4-amino-3-methyl-N,N-diethylaniline hydrochloride,
4-amino-3-methyl-N-ethyl-N-(β-(methanesulfonamido) ethylaniline sesquisulfate hydrate, 4-amino-3-methyl-N-ethyl-N-(β-hydroxyethyl)aniline sulfate,
4-amino-3-β-(methanesulfonamido)ethyl-N,N-diethylaniline hydrochloride and
4-amino-N-ethyl-N-(2-methoxyethyl)-m-toluidine di-p-toluene sulfonic acid.

Development is followed by bleach-fixing, to remove silver or silver halide, washing and drying.

The present invention will be further described in the examples below.

In the following, typical examples of water-dispersible polymeric UV absorbers of the present invention are set forth, but the present invention is not to be constructed as being limited thereto.

| Polymer I.D. | Composition | Weight Ratio |
|---|---|---|
| P-1 | UV-1:Acrylamide:I-2 | 50:40:10 |
| P-2 | UV-1:Butyl Acrylate:I-2 | 50:40:10 |
| P-3 | UV-1:Butyl Acrylate:I-2 | 50:45:5 |
| P-4 | UV-1:Butyl Acrylate:I-2 | 50:48:2 |
| P-5 | UV-2:Butyl Acrylate:I-2 | 51.7:41.0:7.3 |
| P-6 | UV-2:Butyl Acrylate:I-10 | 60:30:10 |
| P-7 | UV-3:Butyl Acrylate:I-2 | 50:45:5 |
| P-8 | UV-3:Ethyl Acrylate:I-2 | 50:45:5 |
| P-9 | UV-3:Ethyl Acrylate:I-6 | 50:45:5 |
| P-10 | UV-4:Butyl Acrylate:I-2 | 50:45:5 |
| P-11 | UV-5:Butyl Acrylate:I-2 | 50:45:5 |
| P-12 | UV-1:UV-3:Butyl Acrylate:I-2 | 25:25:45:5 |
| P-13 | UV-1:UV-3:Butyl Acrylate:I-2 | 15:35:45:5 |
| P-14 | UV-7:Butyl Acrylate:I-2 | 60:35:5 |
| P-15 | UV-7:Ethyl Acrylate:I-2 | 60:35:5 |
| P-16 | UV-7:Ethyl Acrylate:I-6 | 60:35:5 |
| P-17 | UV-7:Butyl Acrylate:I-10 | 60:35:5 |
| P-18 | UV-7:Butyl Acrylate:I-11 | 55:40:5 |
| P-19 | UV-10:Butyl Acrylate:I-2 | 60:35:5 |
| P-20 | UV-10:Ethyl Acrylate:I-2 | 60:35:5 |
| P-21 | UV-10:Ethyl Acrylate:I-6 | 60:35:5 |
| P-22 | UV-10:Butyl Acrylate:I-10 | 60:35:5 |
| P-23 | UV-10:Butyl Acrylate:I-11 | 55:40:5 |
| P-24 | UV-12:UV-11:Butyl Acrylate:I-2 | 20:30:45:5 |
| P-25 | UV-12:UV-11:Butyl Acrylate:I-2 | 25:25:40:10 |
| P-26 | UV-12:UV-11:Butyl Acrylate:I-2 | 35:15:45:5 |
| P-27 | UV-18:Butyl Acrylate:I-2 | 60:35:5 |
| P-28 | UV-14:Butyl Acrylate:I-10 | 50:45:5 |
| P-29 | UV-20:Butyl Acrylate:I-2 | 50:45:5 |
| P-30 | UV-23:Butyl Acrylate:I-2 | 60:35:5 |
| P-31 | UV-24:Butyl Acrylate:I-6 | 60:35:5 |
| P-32 | UV-26:Butyl Acrylate:I-2 | 50:45:5 |
| P-33 | UV-10:Butyl Acrylate:I-16 | 50:40:10 |
| P-34 | UV-16:Butyl Acrylate:I-2 | 60:35:5 |

EXAMPLE 1

Preparation of polymer dispersion P-1

Terpolymer of 2-hydroxy-4(4'-vinylbenzyloxyphenyl benzotriazole(UV-1), acrylamide, and sodium salt of 2-acryloamido-2-methyl-1-propane sulfonic acid (50/40/10 by weight)

In a 250 mL 3-neck flask equipped with condenser, nitrogen inlet, and mechanical stirrer was charged with 5 g of UV-1, 4 g of acrylamide, 1 g of sodium salt of 2-acryloamido-2-methyl-1-propane sulfonic acid, 6.42 g of 10% NaOH, 60 mL of methanol and 10 mL of deionized water. The mixture was purged with nitrogen for 30 mins. while heating to 80° C. 0.2 g of 2-azobiscyanovaleric acid in 1 mL 10% NaOH was added to initiate the polymerization. Three hours later, same amount of initiator was added and polymerized one more hours. The solution was poured into a hot distilled water (180 mL) dropwisely with vigorous stirring. A polymer dispersion was obtained which was dialyzed overnight to remove the organic solvent.

The clean dispersion was concentrated to 3.2% solid by diafiltration. The Z average particle size measured by Malverns'sAutosizer II was 135 nm. Yield was 98%.

EXAMPLE 2

Preparation of polymer dispersion P-5

This example demonstrates the method of adjusting the particle size of polymeric UV dispersion Terpolymer of 2-hydroxy-(5-methacryloxyethylphenyl benzotriazole(UV-2), n-butyl acrylate, and sodium salt of 2-acryloamido-2-methyl-1-propane sulfonic acid (51.7/41.0/7.3 by weight).

In a 250 mL 3-neck flask equipped with condenser, nitrogen inlet, and mechanical stirrer was heated in a constant temperature bath at 80° C. A monomer solution comprised 12.93 g of UV-2, 10.25 g of n-butyl acrylate, 3.17 g of sodium salt of 2-acryloamido-2-methyl-1-propane sulfonic acid, 0.5 g of 2-azobisisobutylnitrile and 100 mL N,N,-dimethylforamide was pumped into the reator over three hours. 0.25 g 2-azobisisobutylnitrile was post-added and polymeized overnight. The polymer solution obtained was splitted to two halfs. One half was diluted with 104 mL of THF and dispersed in 500 ML hot water with vigorous stirring (process A). The other half was diluted with 187 mL THF and dispersed in 750 nm hot water (process B). The dispersions were dialyzed overnight. The particle size the of polymer dispersion from these two processes were 145 nm and 87 nm respectively. Yield was 97.8% total.

EXAMPLE 3

Preparation of polymer dispersion P-3

This example demonstrate various methods of dispersion and methods of controlling particle size of the dispersion. Terpolymer of 2-hydroxy-4(4'-vinylbenzyloxyphenyl benzotriazole(UV-1), n-butylacrylate, and sodium salt of 2-acryloamido-2-methyl-1-propane sulfonic acid (50/45/5 by weight)

A 1 L 3-neck flask equipped with condenser, nitrogen inlet, and mechanical stirrer was heated in a constant temperature bath at 80° C. under nitrogen for 30 mins. A monomer solution comprised 50 g of UV-1, 45 g of n-butyl acrylate, 5 g of 2-acryloamido-2-methyl-1-propane sulfonic acid, 1 g of 2-azobis-isobutylnitrile and 400 mL N,N,-dimethylforamide was pumped into the reator over three hours. 1 g 2-azobisisobutylnitrile was post-added and polymeized overnight. The polymer dispersion can be obtained by either dispersing polymer solution into hot water or adding water to the polymer solution until phase inversion occur. This is demonstrated as follows. Polymer solution obtained above (20% solid) was divided into three portions and diluted with methanol to 10, 7.5 and 5.0% solid. Each polymer solution was further divided to two parts. Polymer dispersion was formed by two methods(A and B). In method A, polymer solution at various % solid was added to three times by volume of hot water with vigorous stirring. In method B, enough hot water was added to the polymer solution at various % solid until phase inversed and a stable dispersion was obtained. The polymer dispersion obtained was dialyzed overnight and their particle sizes are shown in Table I. Total yield was 96%.

TABLE I

| Particle Size of Polymer Dispersion of Polymer (P-3) by Methods A and B | | |
|---|---|---|
| % Solid | Method | Particle Size (nm) |
| 10 | A | 190 |
| 7.5 | A | 124 |
| 5.0 | A | 80 |

TABLE I-continued

| Particle Size of Polymer Dispersion of Polymer (P-3) by Methods A and B | | |
|---|---|---|
| % Solid | Method | Particle Size (nm) |
| 10 | B | 214 |
| 7.5 | B | 150 |
| 5.0 | B | 90 |

EXAMPLE 4

Preparation of polymer dispersion P-28

Terpolymer of 2-hydroxy-(4-methacryloamidophenyl benzotriazole(UV-14), n-butylacrylate, and sodium styrene sulfonate (50/40/10 by weight)

A 1 L 3-neck flask equipped with condenser, nitrogen inlet, and mechanical stirrer was heated in a constant temperature bath at 80° C. under nitrogen for 30 mins. A monomer solution comprised 25 g of UV-15, 20 g of n-butyl acrylate, 5 g of sodium styrene sulfonate, 0.5 g of 2-azobisisobutylnitrile and 200 mL N,N,-dimethylforamide was pumped into the reator over three hours. 0.5 g 2-azobisisobutylnitrile was post-added and polymeized overnight. The polymer solution was cooled to room temperature and poured to 1 L of water. The yellow precipitate was dried in a vacuum oven at 80° C. overnight. 47 g of polymer was obtained.

The polymer was dissolved in acetone to various concentration and dispersed in three times by volume of hot water. The results are shown in Table II.

TABLE II

| % Solid | Method | Particle Size (nm) |
|---|---|---|
| 10 | A | 176 |
| 7.5 | A | 110 |
| 5.0 | A | 77 |

This example illustrate that the polymeric UV absorber prepared by this invention can be isolated as solid and redispersed to form good dispersion.

COMPARISON EXAMPLE

The following examples shows the typical experimental procedure for the preparation of polymeric UV absorber by the emulsion polymerization technique.

COMPARISON EXAMPLE 1

Latex of copolymer of UV-1 and n-Butyl Acrylate (1:2 molar ratio).

In a 12 L 4-neck RB flask equipped with condenser, nitrogen inlet, and mechanical stirrer was charged with 4738 mL deionized water, 25.1 g of Igepon T-77 (sodium N-methyl-N-oleoyltaurate by GAF), and 483 g of acetone. The solution was purged with nitrogen for 30 mins while heated to 80° C. in a constant temperature bath. 7.91 g of ammonium persulfate was added and stirred for 5 mins. A monomer solution comprising 236.9 g of UV-1, 176.9 g of n-butyl acrylate in 4738 g of DMF was pumped into the reactor over six hours. The polymerization was continued for 12 hours. Latex was cooled to room temperature, filtered and dialyzed overnight. Latex was then concentrated to 15.7% with a diafiltration unit. Average particle size is 99 nm. Yield was 95%.

COMPARISON EXAMPLE 2

Latex of copolymer of 2-hydroxy-5-methacryloylphenyl-2-benzotriazole(UV-2), 2-ethoxyethylacrylate, and methacrylic acid 360 mL of deionized water, 3.15 g of a 34% aqueous solution of Aerosol A-103 (trade name for disodium ethoxylated nonylphenol half ester of sulfosuccinic acid), and 40 mL of acetone were mixed in a 1 L 4-neck round bottom flask equipped with an agitator, nitrogen inlet, and a reflux condenser. The flask was immersed in an 80° C. constant temperature bath, and heated for 30 minutes with nitrogen purge. 9.69 g of 2-hydroxy-5-methacryloylphenyl-2-benzotriazole(UV-2) and 4.33 g of 2-ethoxyethyl acrylate, and 0.26 g of methacrylic acid were dissolved in 180 mL of N,N-dimethylformamide. 5.71 g of 5% ammonium persulfate were added to the reactor and stirred for 3 minutes. The monomer solution and another co-feed solution containing 1.05 g of Aerosol A-103, 2.9 g of 5% $Na_2S_2O_8$ and 100 mL deionized water were pumped concurrently into the reactor over 4½ hours after which the reactor was held at 80° C. for 8 hours. Latex was cooled and filtered to remove the coagulum. 9.4 g of coagulum was filtered. Z-average particle size was 253 nm and yield was 34.2%. % solid was 2%.

COMPARISON EXAMPLE 3

Latex of copolymer (specifically, a terpolymer in the present comparison example) of 2-hydroxy-4-methacryloamidophenyl-2-benzotriazole(UV-14), n-butyl acrylate and sodium salt of 2-acryloamido-2-methyl-1-propane sulfonic acid.

120 mL deionized water, 3.68 g of Igepon T-77 (sodium N-methyl-N-oleoyltaurate by GAF), and 12 g of acetone were charged to a 500 mL 4-neck RB flask equipped with condenser, nitrogen inlet, and mechanical stirrer. The solution was purged with nitrogen for 30 mins while heated to 80° C. in a constant temperature bath. 7.91 g of 5% ammonium persulfate was added and stirred for 5 mins. A monomer solution comprising 5.89 of UV-15, 5.13 g of n-butyl acrylate, and 0.92 g sodium salt of 2-acryloamido-2-methyl-1-propane sulfonic acid in 100 g of DMF and a cofeed solution comprising 60 g of deionized water, 1.84 g of Igepon T-77 and 2.2 g of ammonium persulfate were pumped concurrently into the reactor over six hours. Latex coagulated near the end of polymerization. The coagulum could not be redispersed to form latex again.

Advantages

Unlike the traditional dispersion method and emulsion polymerization, surfactant or emulsifier is not required for the dispersion and high energy is not required. The polymer made by the method of the present invention is self-dispersible in water. Surfactants can have adverse effects on the photographic materials, such as high fogging or stainning or causing viscosity increase.

Unlike emulsion polymerization, the dispersion of polymeric UV absorber can be prepared by the method of this invention from any ethyleneically unsaturated UV monomer. This is apparent from the comparison between example 4 and comparison example 3; both of them are derived from UV-14.

The polymeric UV absorber prepared by the method of this invention can be isolated as a solid and redispersed. This is not possible for the polymeric UV absorber prepared by an emulsion polymerization method (for example, as in Comparison Example 3).

As described in examples 2, 3 and 4, it is very easy to adjust the particle size of the final polymer dispersion by method of the present invention. Dispersion with various particle sizes can be obtained from the same polymer by adjusting the concentration of the polymer solution prior to the dispersion or the amount of ionic comonomer. For emulsion polymerization, the only tool to adjust the particle size is by adjusting the amount of surfactant.

Photographic Evaluation

Polymeric UV absorbing agents prepared by example 1 of this invention and comparison example 1 were incorporated in a color photographic paper with layer arrangements shown below. Experiment were conducted to show how the of the polymeric UV absorbing agents of the invention improved the light-induced discoloration of color-forming dyes.

For comparison purpose, the following conventional check UV dispersion are also prepared. This is a conventional dispersion composed of Tinuvin 328 (0.85), Tinuvin 326(0.15) (from Ciba-Geigy), 1,4-Cyclohexylenedimethylene bis(2-ethylhexanoate)(0.333), 2,5-bis(1,1,3,3-tetramethylbutyl)-1,4-benzenediol (0.114), 10% Alkanol LC(0.555), and TCG2 Gel(0.708). The numbers inside parenthesis are the relative weight ratio. The dispersion was prepared by the colloid mill process in the presence of gelatin as known in the art. The average particle size is 275 nm.

The following multilayer photographic element was constructed using the comparison and conventional check dispersions, and UV absorbing polymers prepared and directly dispersed according to the methods of the present invention:

| Layer No. | Layer Name | Ingredients (mg/ft$^2$) unless indicated |
|---|---|---|
| 8 (Optional) | Protective Layer | 125 Gelatin |
| | | 1.05 Alkanol XC (a surfactant from DuPont) |
| | | 0.394 FT-248 (a surfactant from DuPont) |
| | | 12.87 BVSME (a hardner) |
| 7 | UV Layer | 61 Gelatin |
| | | 0.17 mmole/ft$^2$ UV absorbing agent |
| 6 | Interlayer | 2.0 Scavenger 1 |
| | | 100 Gel |
| 5 | Cyan Layer | 100 Gelatin |
| | | 39.3 Cyan Coupler |
| | | 0.54 Scavenger 1 |
| | | 16.7 Red sensitized AgCl Emulsion |
| | | 21.44 Coupler Solvent |
| 4 | Interlayer | 65.0 Gelatin |
| | | 4.02 Scavenger 1 |
| 3 | Magenta Layer | 115.0 Gelatin |
| | | 36.14 Magenta Coupler |
| | | 19.2 Magenta Stabilizer |
| | | 26.65 Green sensitized AgCl Emulsion |
| | | 14.25 Coupler Solvent |
| 2 | Interlayer | 70.0 Gelatin |
| | | 8.75 Scavenger 1 |
| 1 | Yellow Layer | 140.0 Gelatin |
| | | 68.03 Yellow Coupler |
| | | 23.63 Blue Sensitized AgCl Emulsion |
| | | 0.88 Scavenger 2 |
| Support | sublayer 1 | Resin Coat:Titanox and Optical Brightner Dispersed in Polyethylene |
| | sublayer 2 | Paper |
| | sublayer 3 | Resin Coat:Polyethylene |

The photographic papers with the arrangement described above were processed by the well-known RA-4 process (see Research Disclosure I).

Magenta Coupler
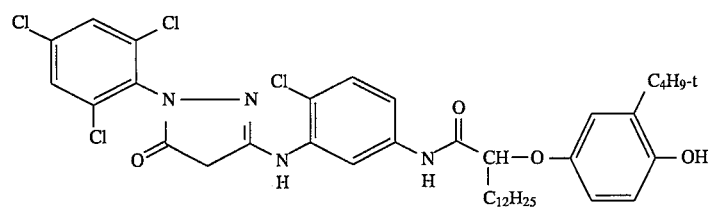
Yellow Coupler
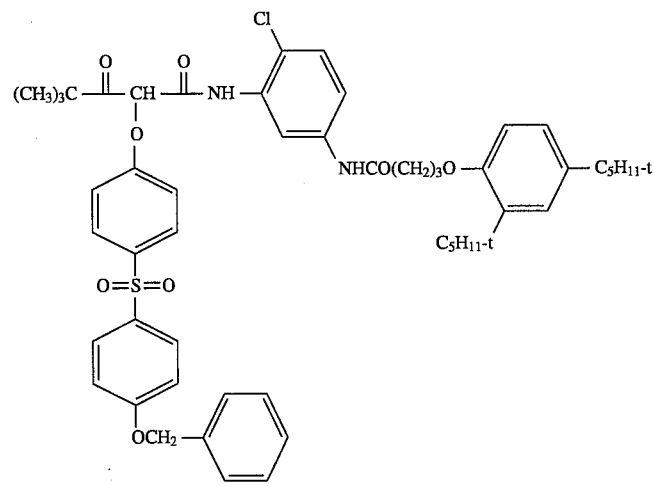
Cyan Coupler
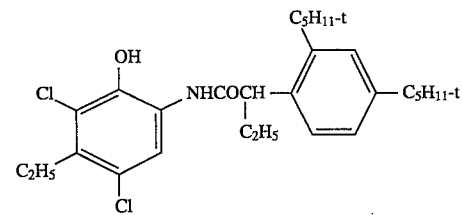
Scavenger 1
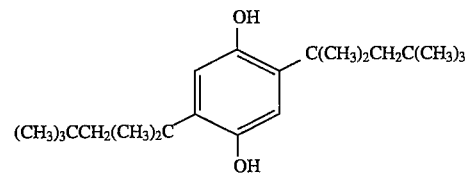
Scavenger 2
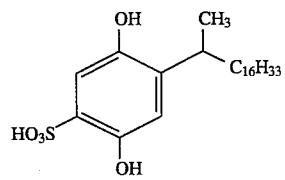

Stabilizer

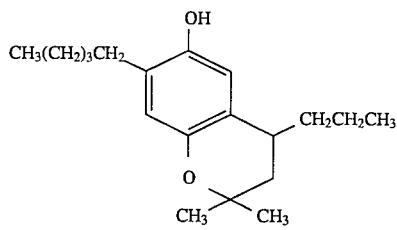

The photographic materials with the layer structures shown above were exposed with a step tablet wedge to three different colors (red, green, red)on a sensitometer and subsequently processed by RA-4 process to provide cyan, magenta, and yellow colors. The light stability of these coatings are carried out by the typical Xenon fadeometer exposure with Xe arc lamp as light source at 25° C. for two weeks. The samples were irradiated at a distance such that the irradiance on the sample was 50 Klux. Dye density loss from the original density of 1.0 was measured and the data was used as the index for the image dye stability. Since human eye is most sensitive to magenta color, the magenta dye stability is the most important among these three colors. The results are shown in Table 3.

TABLE 3

| Sample | Cyan | Magenta | Yellow | Remarks |
|---|---|---|---|---|
| Conventional Check | −0.04 | −0.24 | −0.27 | Comparison |
| Comparison Example 1 | −0.01 | −0.28 | −0.23 | Comparison |
| Example 1 | −0.02 | −0.16 | −0.10 | Invention |

Table 3 shows that the polymeric UV dispersion made by this invention has much better dye fade protection than the conventional check and the polymeric UV absorber prepared by emulsion polymerization.

The preceding examples are set forth to illustrate specific embodiments of this invention and are not intended to limit the scope of the compositions or materials of the invention. It will be understood that variations and modifications can be effected within the spirit and scope of the invention.

We claim:

1. A photographic element containing a polymeric UV absorbing compound, which compound comprises UV absorbing monomeric units formed from at least one UV absorbing ethylenically unsaturated monomer and at least 0.05 weight percent of ionic units which have an ionizable group which is ionized at all pH values between 5 to 10 and are formed from at least one ethylenically unsaturated monomer containing such an ionizable group and selected from the group consisting of:

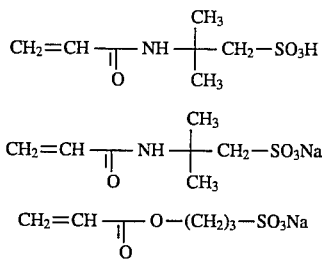

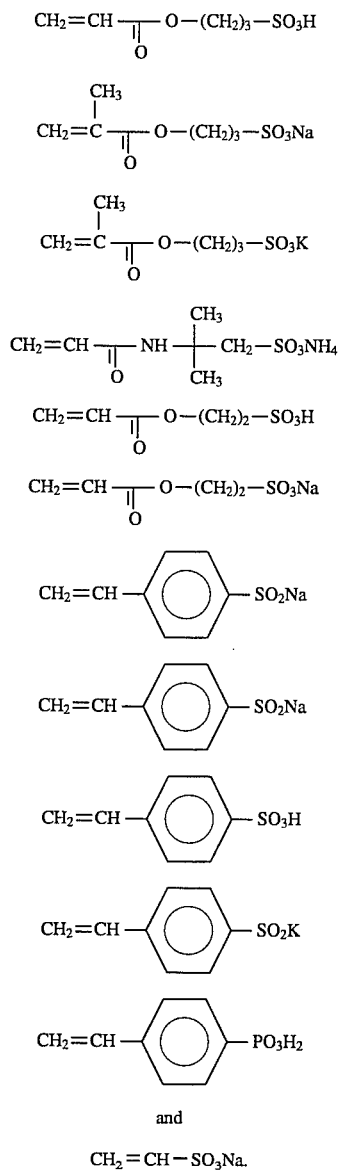

and $CH_2=CH-SO_3Na$.

2. A photographic element containing a polymeric UV absorbing compound, which compound comprises UV absorbing monomeric units formed from at least one UV absorbing ethylenically unsaturated monomer and at least 0.05 weight percent of ionic units which have an ionizable group which is ionized at all pH values between 2 to 14 and are formed from at least one ethylenically unsaturated monomer containing such an ionizable group and selected from the group consisting of:

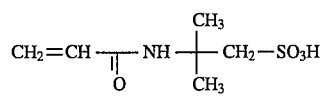
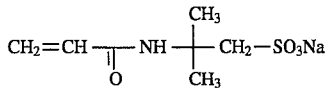
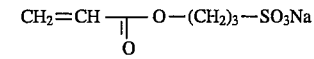
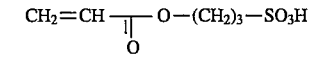
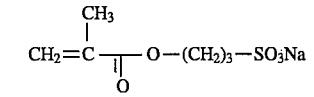
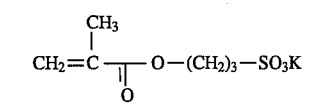
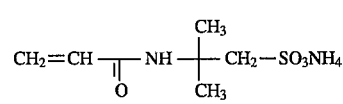
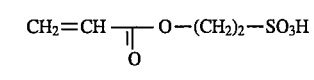
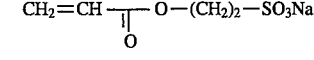
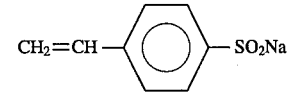
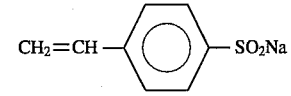
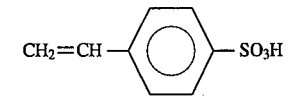
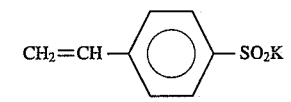
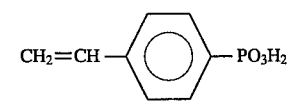

and

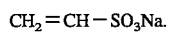

3. A photographic element containing a polymeric UV absorbing compound, the UV absorbing compound being dispersed in the photographic material without surfactants and which UV absorbing compound comprises UV absorbing monomeric units formed from at least one UV absorbing ethylenically unsaturated monomer and from 0.05 to 20 weight percent of ionic units which have an ionizable group which is ionized at all pH values between 2 to 14 and are formed from at least one ethylenically unsaturated monomer containing such an ionizable group and selected from the group consisting of:

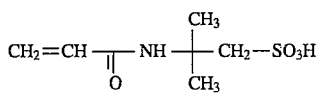
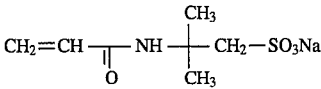
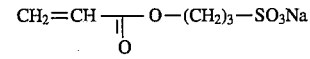
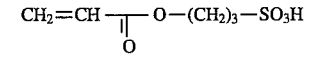
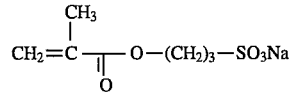
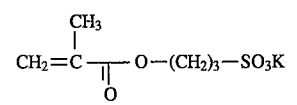
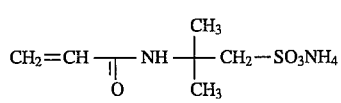
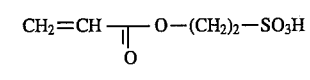
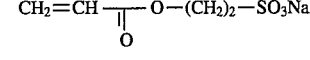
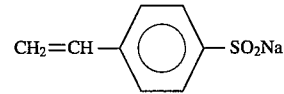
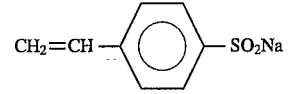
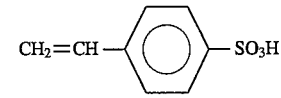
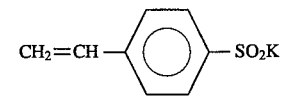
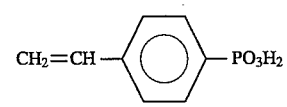

and

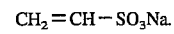

4. A photographic element containing a binder and polymeric UV absorbing compound in the binder, the UV absorbing compound having been directly dispersed in water to form a latex and having been prepared by solution polymerization of a mixture of at least one ethylenically unsaturated UV absorbing monomer and at least one ethylenically unsaturated ionic monomer containing an ionizable group which is ionized at all pH values between 2 to 14 and selected from the group consisting of:

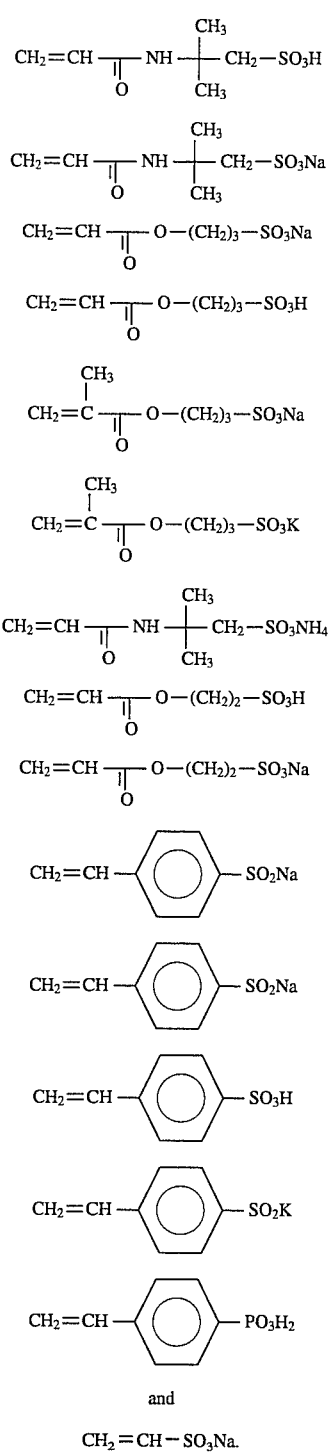

and

CH₂=CH—SO₃Na.

5. A method of preparing a photographic element, the method comprising directly dispersing a polymeric UV absorbing compound in water to form a latex, and combining the latex with a binder composition and coating the composition to form a layer of the photographic element, the polymeric DV absorbing compound comprising UV absorbing monomeric units formed from at least one UV absorbing ethylenically unsaturated monomer and at least 0.05 weight percent of ionic units which have an ionizable group which is ionized at all pH values between 5 to 10 and are formed from at least one ethylenically unsaturated monomer containing such an ionizable group and selected from the group consisting of:

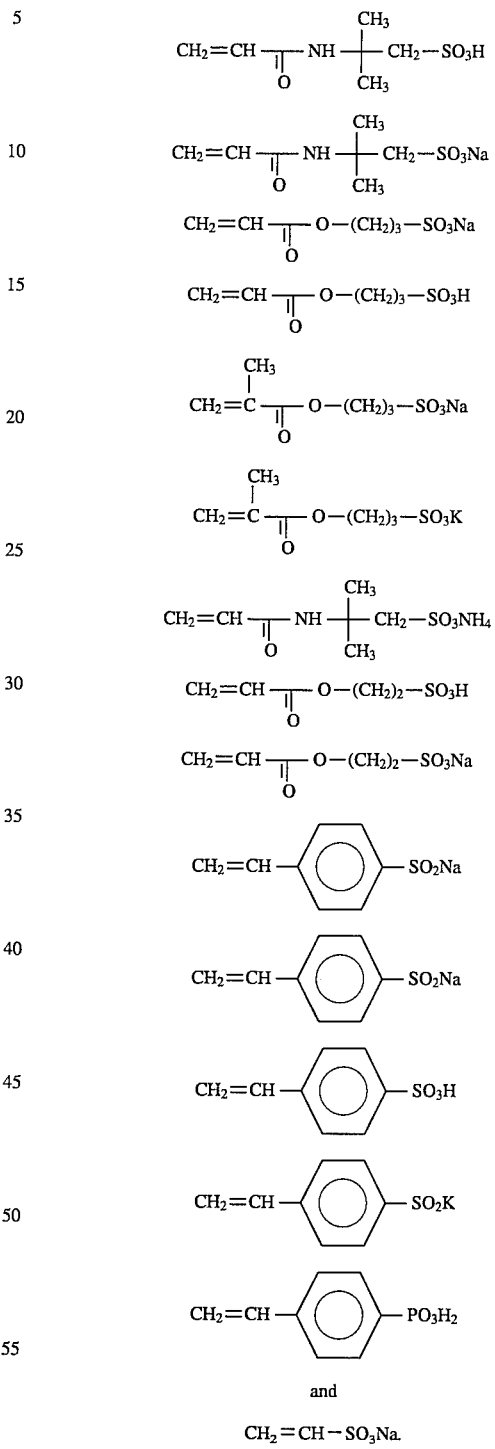

and

CH₂=CH—SO₃Na.

6. A method of preparing a photographic element, the method comprising solution polymerizing a mixture of at least one ethylenically unsaturated UV absorbing monomer and at least one ethylenically unsaturated ionic monomer containing an ionizable group that is ionized at all pH between 2 and 14 and selected from the group consisting of:

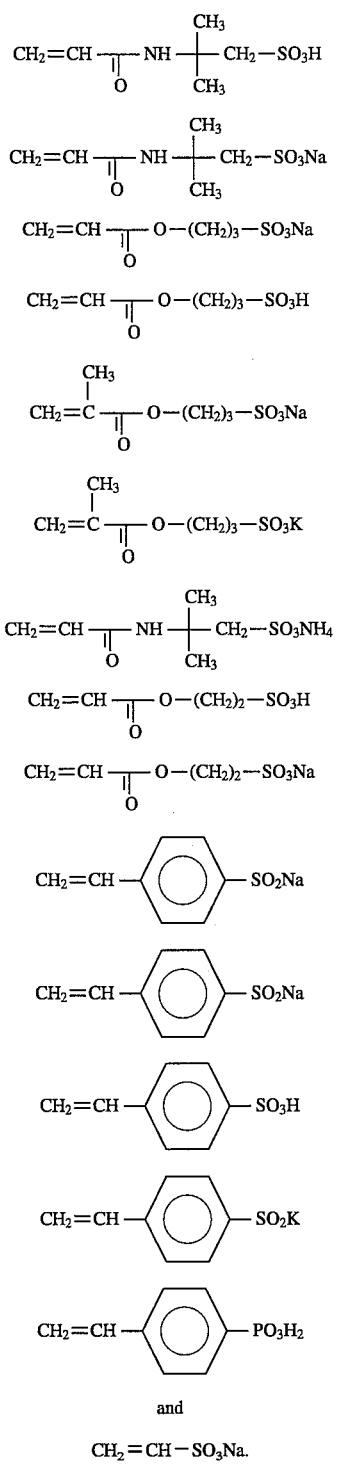

and $CH_2=CH-SO_3Na$.

such that the polymeric UV absorbing compound contains no more than 10 weight percent of units formed from the ionic monomer, then directly dispersing the polymeric UV absorbing compound in water to form a latex, and combining the latex with a binder composition and coating the composition to form a layer of the photographic element.

7. A photographic element according to claim 1 wherein the UV absorbing compound is present as a latex dispersion and comprises up to 20 weight percent of the ionic units.

8. A photographic element according to claim 2 wherein the ionic units are present in an amount of from 1 to 5 weight percent of the polymeric UV absorbing compound.

9. A photographic element according to claim 1 wherein the UV absorbing monomeric units are selected from units containing a phenyl substituted triazole or a phenyl substituted triazine.

10. A photographic element according to claim 1 wherein the UV absorbing monomeric units are units which contain a 2-hydroxyphenylbenzotriazole.

11. A photographic element according to claim 1 wherein the ionizable group of the ionic units is a sulfonate, sulfate, sulfinate, or phosphate.

12. A photographic element according to claim 4 wherein the UV absorbing monomeric units are units which contain a 2-hydroxyphenylbenzotriazole.

13. A photographic element according to claim 4 wherein the ionizable group of the ionic units is a sulfonate, sulfate, sulfinate.

14. A photographic element according to claim 4 wherein the binder is a gelatin composition.

15. A photographic element according to claim 1 wherein the element contains a compound capable of forming a colored dye upon reaction with oxidized color developer during processing.

16. A photographic element according to claim 15 wherein the compound capable of forming a colored dye, is a color coupler which couples with the oxidation product of an aromatic amine developer.

17. A method according to claim 5 wherein the ionizable group of the ionic units is ionized at all pH values between 2 to 14.

18. A method according to claim 17 wherein the latex is added to the binder composition.

19. A method according to claim 17 wherein the ionic units are present in an amount of from 1 to 5 weight percent of the polymeric UV absorbing compound.

20. A method according to claim 5 wherein the ionizable group of the ionic units is a sulfonate, sulfate, sulfinate, or phosphate.

21. A method according to claim 17 wherein the UV absorbing monomeric units are units which contain a 2-hydroxyphenylbenzotriazole and the ionizable group of the ionic units is a sulfonate, sulfate, or sulfinate.

22. A method according to claim 17 wherein the polymeric UV absorbing compound contains no more than 10 weight percent of units formed from the ionic monomer.

23. A method according to claim 22 wherein the polymeric UV absorbing compound which is formed contains from 1 to 5 weight percent of the polymeric UV absorbing compound.

24. A method according to claim 6 wherein the binder composition is a gelatin composition.

25. A photographic element according to claim 6 wherein the UV absorbing monomeric units are units which contain a 2-hydroxyphenylbenzotriazole.

26. A photographic element according to claim 6 wherein the ionizable group of the ionic units is a sulfonate, sulfate sulfinate.

* * * * *